(12) United States Patent
Cole

(10) Patent No.: US 8,765,074 B2
(45) Date of Patent: Jul. 1, 2014

(54) MULTIPLE SCENT DELIVERY DEVICE

(76) Inventor: Brian D. Cole, Wilmington, OH (US)

( * ) Notice: Subject to any disclaimer, the term of this patent is extended or adjusted under 35 U.S.C. 154(b) by 0 days.

(21) Appl. No.: 13/535,958

(22) Filed: Jun. 28, 2012

(65) Prior Publication Data

US 2014/0154149 A1  Jun. 5, 2014

(51) Int. Cl.
*A61L 9/03* (2006.01)
(52) U.S. Cl.
USPC ............... 422/307; 422/120; 422/123; 239/34
(58) Field of Classification Search
USPC ................ 422/307, 120–125; 239/53–57, 34; 126/120
See application file for complete search history.

(56) References Cited

U.S. PATENT DOCUMENTS

| | | | |
|---|---|---|---|
| 4,566,055 A * | 1/1986 | Klees et al. | 362/162 |
| 4,781,895 A * | 11/1988 | Spector | 422/125 |
| 6,038,805 A | 3/2000 | Smidtke | |
| 6,328,935 B1 | 12/2001 | Buccellato | |
| 7,249,947 B2 | 7/2007 | Papai | |
| 7,568,912 B2 | 8/2009 | Kubicek et al. | |
| 7,883,677 B2 | 2/2011 | Palozzi | |
| 2006/0147338 A1 | 7/2006 | Nakatsu et al. | |
| 2008/0318177 A1 * | 12/2008 | Requejo et al. | 431/291 |
| 2009/0200393 A1 | 8/2009 | Avelar | |
| 2009/0291400 A1 | 11/2009 | Levy | |

* cited by examiner

*Primary Examiner* — Sean E Conley
(74) *Attorney, Agent, or Firm* — R. William Graham

(57) ABSTRACT

A multiple scent delivery device includes a support housing having a plurality of holes therein and having an upper end and a lower end, a heating source removably connected to a lower end of said upwardly disposed support housing, a cone shaped inner flue operably disposed within the support housing having a plurality of holes therein and having an upper end and a lower end and an upper container removably disposed on the upper end of support housing in spaced-apart relationship above from the heating source for retaining an aromatic substance, whereby heat generated induces the retained aromatic substance within the upper container to disperse into the ambient air.

18 Claims, 4 Drawing Sheets

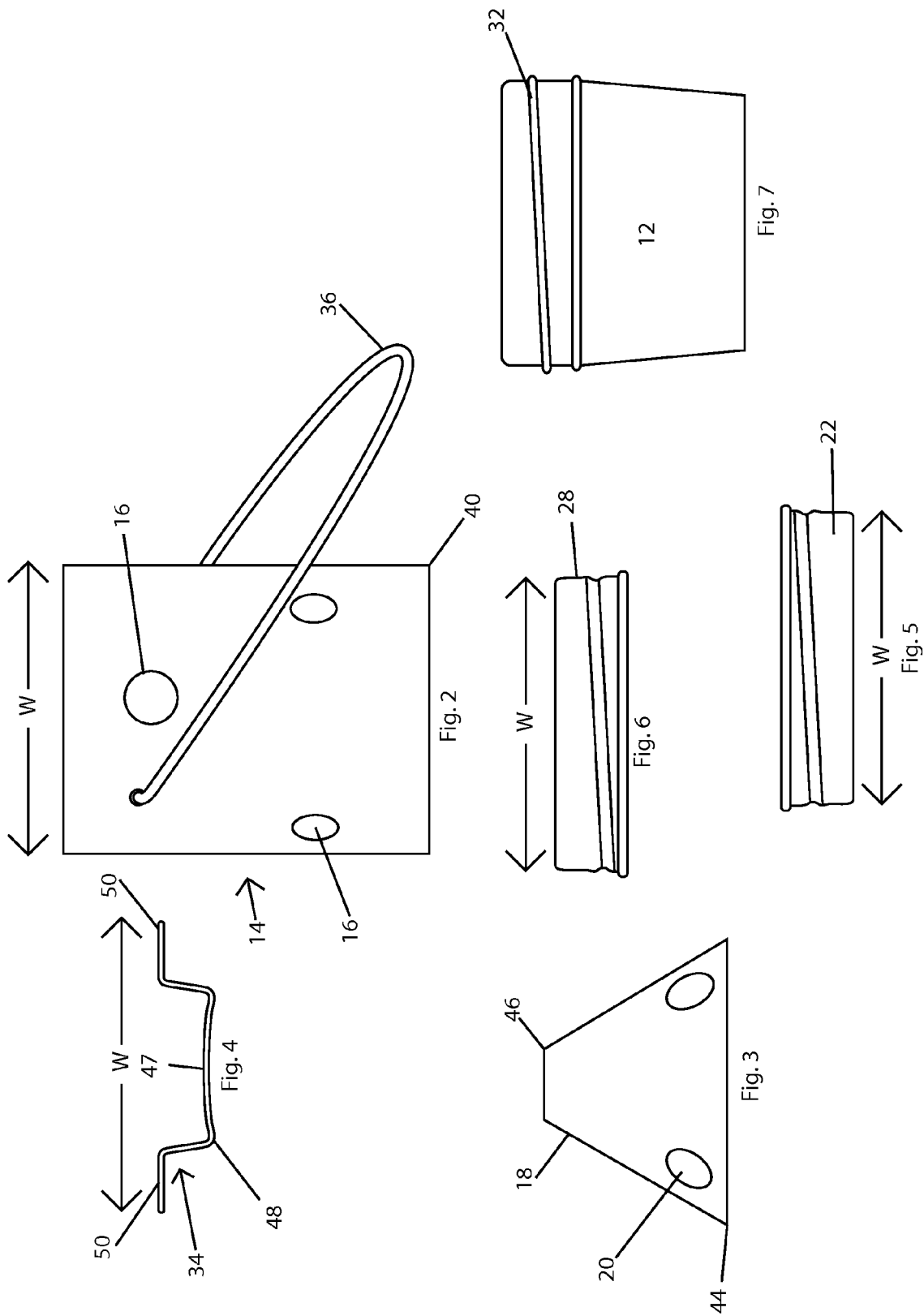

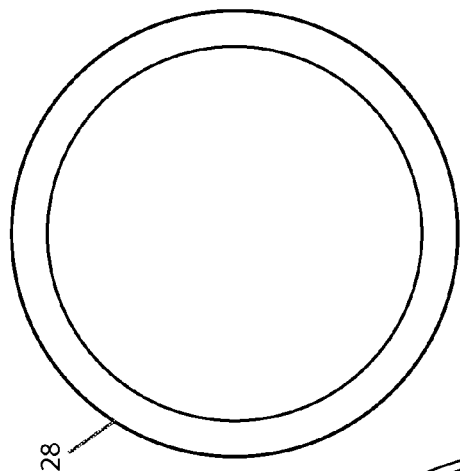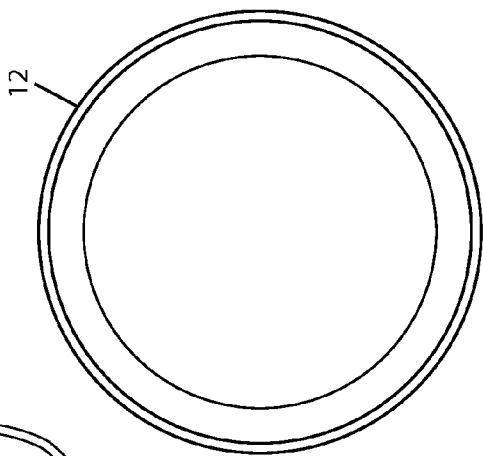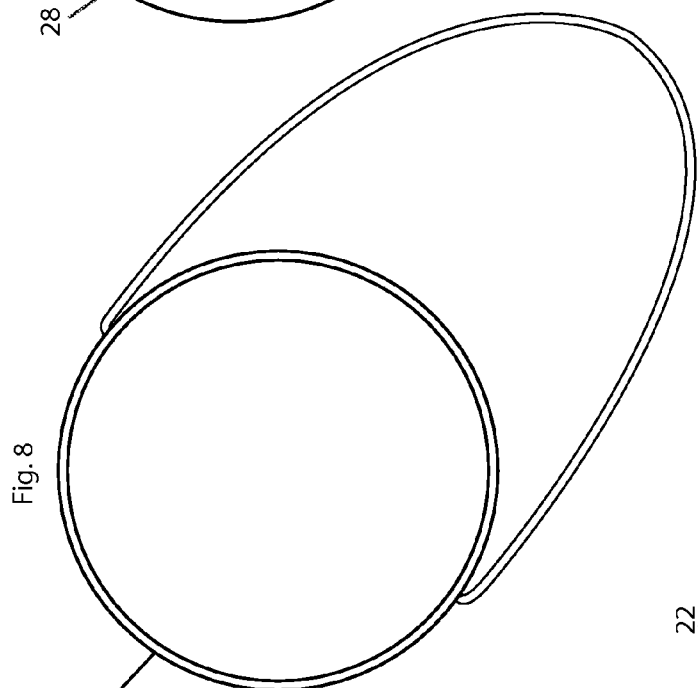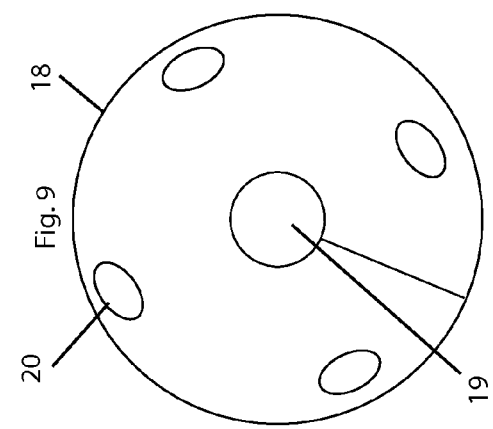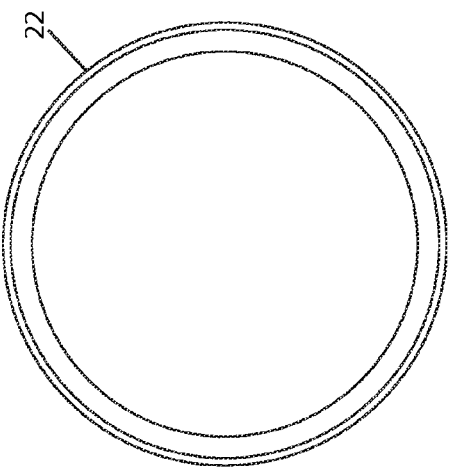

MULTIPLE SCENT DELIVERY DEVICE

BACKGROUND OF THE INVENTION

1. Field of the Invention

The invention pertains to the field of scent delivery devices. More particularly, but not by way of limitation, the invention pertains to a portable and convenient form of multiple scent delivery device for use as a deer lure.

2. Description of Related Art

There have been many aroma devices in the past. A common scenting device is a scented wax candles are commonly used as aroma dispensers, such candles are generally inefficient and inadequate for such purposes. During use, most of the heat generated by the candle flame travels upwardly away from the wax portion of the candle below and little of the heat is available to drive the aromatic substances out of the melted wax.

An improvement of the scented candle includes a dispenser having a flame source for providing heat, an open, porous annular ceramic substrate adapted for absorbing and reversibly retaining a quantity of at least one aromatic fluid therein. A support structure is provided for holding the porous substrate in a coaxial spaced-apart relationship above the flame source, whereby heat generated by the flame source induces the retained aromatic fluid within the substrate to disperse into the ambient air. Many devices for dispersion of such scents include various types of passive dispersion and active dispersion relying on heating and/or evaporation of the liquid scent with or without an air mover.

In the case of animal lures, various aromatic materials have been used. In recent times, deer hunters have often had recourse to the use of urine scents. For example, the urine of a doe in heat is often used to attract bucks to the location where the hunter is located.

While there are many devices which exist, there remains a need to improve the art. The invention improves on the state of the art of such devices and fulfills the need for an active dispersion relying on heating and/or evaporation of the liquid scent that is compact, convenient, efficient, easy to use, and includes anchoring means for holding it in position for its intended purposes.

SUMMARY OF THE INVENTION

It is an object to improve scenting devices.
It is another object to provide a multiple scenting device.
It is still another object to provide a scenting device which is well suited for luring animals, such as deer.

The present invention is generally directed to a multiple scent delivery device. The multiple scent delivery device includes a heating source removably connected to an upwardly disposed support housing having a plurality of holes therein, a cone shaped inner flue disposed within the support housing having a plurality of holes therein, and an upper container removably disposed on the support housing in spaced-apart relationship above from the heating source for retaining an aromatic substance, whereby heat generated (e.g., by lit candle) induces the retained aromatic substance within the upper container to disperse into the ambient air. Thus, upon the heating source being activated, the substance is warmed in a manner to cause an efficient and an effective scent (or optionally an air freshener) with the flexibility and advantages allowing the user to select and change to any desired scent (or aroma). In an embodiment, the heating element includes a jar having a candle which can be scented and lit. A jar connecting collar can be friction fit or affixed within the support housing and include a threaded internal surface to threadably receive a threaded upper end of the candle jar.

The multiple scent delivery device can include a press fit locator for positionally maintaining the cone shaped inner flue in a predetermined position within the support housing. The housing can include a hanger member to enable the multiple scent delivery device to be hung or suspended from a generally horizontal member, which can be a tree branch for example.

The multiple scent delivery device can include a quantity of at least one aromatic fluid. The aromatic fluid disperses in a vaporous form into the ambient air when heated by a candle flame from below. Alternatively, the upper container can be used to efficiently deliver fragrance at lower levels when the candle is not lit.

The support housing can be a cylinder and includes a lower end and an upper end, with at least one air inlet hole in a cylinder wall adjacent the lower end and one inlet hole adjacent the upper end. The cone shaped inner flue has the holes adjacent a lower end of the cone shaped inner flue. The press fit locator and include a width configured to friction fit within the support housing and can include a central open surface to receive an upper end of the cone shaped inner flue in a contacting manner. The upper container can include a diameter width configured to friction fit within the support housing.

BRIEF DESCRIPTION OF THE DRAWINGS

Various embodiments of the invention are described in detail below with reference to the drawings, in which like items are identified by the same reference designation, wherein:

FIG. 2 is a side view of a support housing of the instant invention;
FIG. 3 is a side view of a cone shaped flue of the instant invention;
FIG. 4 is a side view of a retaining member of the instant invention;
FIG. 5 is a side view of an upper container of the instant invention;
FIG. 6 is a side view of a connecting collar of the instant invention;
FIG. 7 is a side view of a candle jar of the instant invention;
FIG. 8 is a top view of a support housing of the instant invention;
FIG. 9 is a top view of a cone shaped flue of the instant invention;
FIG. 10 is a top view of a retaining member of the instant invention;
FIG. 11 is a top view of an upper container of the instant invention;
FIG. 12 is a top view of a connecting collar of the instant invention;
and
FIG. 13 is a top view of a candle jar of the instant invention.

DETAILED DESCRIPTION OF THE INVENTION

Figure 1:
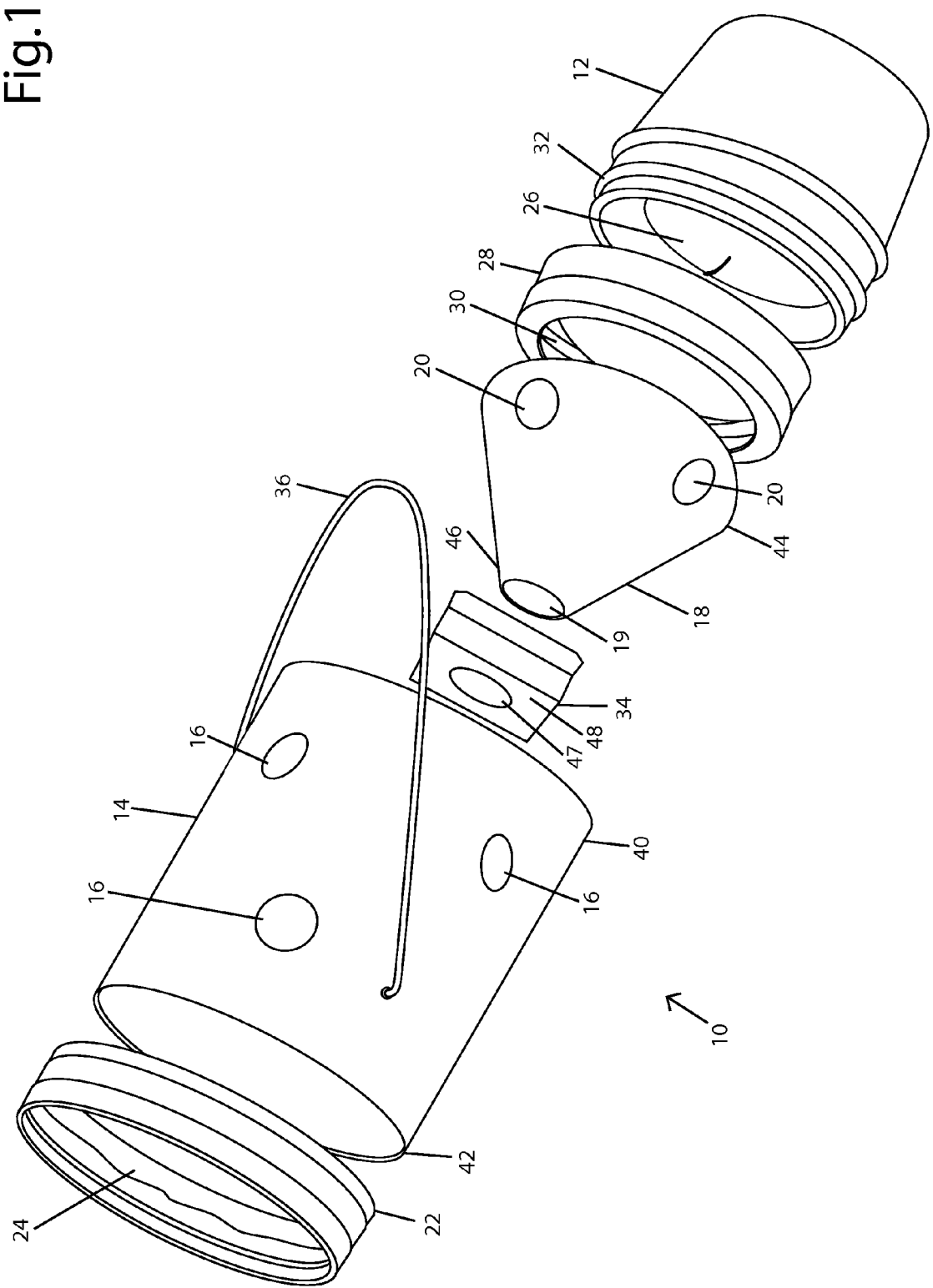
FIG. 1 is an exploded assembly diagram of an aroma dispenser for one embodiment of the present invention.
Figure 14:
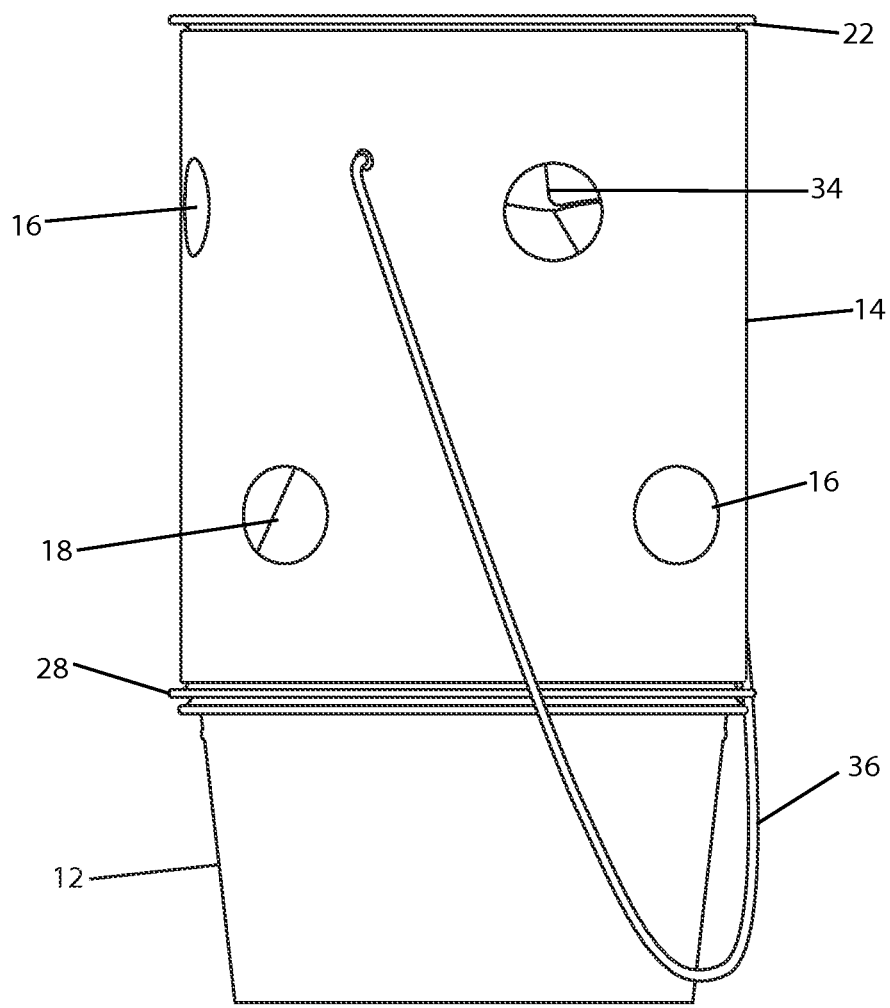
FIG. 14 is a side view of the invention.

The present invention is generally directed to an aroma dispenser constructed in a manner to provide a simple and inexpensive arrangement for dispersing a quantity of an aromatic or scent-producing fluid into ambient air and is generally designated by the numeral 10. The multiple scent delivery device 10 includes a heating source 12 removably connected to an upwardly disposed support housing 14 having a plurality of holes 16 therein.

A cone shaped inner flue 18 is disposed within the support housing 14 having a plurality of holes 20 therein. An upper container 22 is removably disposed on the support housing 14 in spaced-apart relationship above from the heat source 12 for retaining an aromatic substance 24, whereby heat generated from the heat source 12 (e.g., by lit candle) induces the retained aromatic substance 24 within the upper container 22 to disperse into the ambient air. Thus, upon the heating source 12 being activated, the aromatic substance 24 is warmed in a manner to cause an efficient and an effective scent (or optionally an air freshener) with the flexibility and advantages allowing the user to select and change to any desired scent (or aroma).

In an embodiment, the bottom heating source 12 includes a jar having a candle 26 which can be scented and lit to provide an additional scent or aroma. A jar connecting collar 28 can be friction fit or affixed within the support housing 14 and include a threaded internal surface 30 to threadably receive a threaded upper end 32 of the candle jar 12.

The multiple scent delivery device 10 can include a press fit locator 34 for positionally maintaining the cone shaped inner flue 18 in a predetermined position within the support housing 14. The support housing 14 can include a hanger member 36 to enable the multiple scent delivery device 10 to be hung or suspended from a generally horizontal member, such as a tree branch, for example.

The multiple scent delivery device 10 can include a quantity of at least one aromatic fluid 24. It is contemplated, though not shown, that the container 22 can include a divider formed therein to enable multiple scents to disposed in separate sections thereof. The aromatic fluid 24 disperses in a vaporous form into the ambient air when heated by a candle flame of candle 26 from below. The lit candle 26 can also include a scented wax or oil based substance for example. Alternatively, the substance 24 can be used to efficiently deliver fragrance at lower levels when the candle 26 is not lit.

The support housing 14 can be in the form of a cylinder and includes a lower end 40 and an upper end 42, with at least one air inlet hole 16 in a cylinder wall adjacent the lower end 40 and one inlet hole 16 adjacent the upper end 42. The cone shaped inner flue 18 has holes 20 adjacent a lower end 44 and has a central opening 19 which extends from end 44 through upper end 46.

The press fit locator 34 includes a diameter width proximate width W configured to friction fit within the support housing 14 having an inner diameter width W and can include a central open surface 47 to receive upper end 46 of the cone shaped inner flue 44 in a contacting manner. The press fit locator 34 is seen in FIG. 4 as having a U shaped mid section 48 with laterally extending flanges 50. The upper support container 22 can include a diameter width proximate width W configured to friction fit within the support housing.

The multiple scent delivery device 10 provides for candle 26 with a wick and a support structure for supporting a porous substrate. The container 22 retains the porous substrate in a position above and in close proximity to the candle wick and is configured to retain a quantity of an aromatic fluid 24 therein. Through evaporative effects induced by ambient heat and/or heat generated by the lit candle 26 for accelerating evaporation, the aromatic fluid 24 is converted into vapors which diffuse into the ambient air for a pleasant aroma.

The multiple scent delivery device 10 can be composed of a rigid, durable material, preferably having refractory and flame resistant properties including, but not limited to, ceramic, metal, glass, stone, and alumina. The multiple scent delivery device 10 is constructed with the advantage of permitting the user to change or modify aromas as desired, mix one or more aromatic substances depending on the user's preferences and/or to adjust the rate of aroma delivery into the ambient air by controlling the amount or concentration of the aromatic fluid furnished to the substrate, and heat generated by a lit candle 26 associated therewith. In addition, the multiple scent delivery device 10 is for use with various types of candles scented or non-scented, and allows for easy replacement of the candle upon exhaustion. The cost effective and efficient manner by which these dispensers are constructed and implemented, makes such dispensers especially suitable for household use.

As can be seen from the drawing figures, my invention is a multiple scent delivery device 10 which is portable and in one embodiment is a self-contained deer lure with parts that are easy to assemble for use and are also capable of being packed into a small and easily carried configuration. The particular configuration provides for a unique design which provides air flow into the support housing 14 through holes 16 and then the cone 18 can be oriented in a way to permit air flow through holes 20, yet not coaxially align the holes 16 and 20 thus prevent light from being seen as well as deter the candle 26 from being blown out in windy conditions.

Although various embodiments of the invention have been shown and described, they are not meant to be limiting. Those of skill in the art may recognize various modifications to these embodiments, which modifications are meant to be covered by the spirit and scope of the appended claims. For example, the multiple scent delivery device 10 can be of any desired and practical shape and so forth or the lid of the container may include other configurations such as including vents for permitting continuous aroma dispensing.

What is claimed is:

1. A multiple scent delivery device having an aromatic substance, which includes:
    a support housing having a plurality of holes therein and having an upper end and a lower end;
    a heating source removably connected to a lower end of said support housing;
    a cone shaped inner flue operably disposed within said support housing having central opening extending through from an upper end through a lower end and a plurality of holes in a side of said cone therein and having an upper end and a lower end; and
    an upper container removably disposed on said upper end of support housing in spaced-apart relationship above from said heating source receiving the aromatic substance, whereby heat generated induces the retained aromatic substance within said upper container to disperse into the ambient air.

2. A multiple scent delivery device of claim 1, wherein said cone shaped inner flue is removably disposed within said support housing.

3. A multiple scent delivery device of claim 1, wherein said heating source includes a lit candle.

4. A multiple scent delivery device of claim 3, wherein said lit candle includes a scented material.

5. A multiple scent delivery device of claim 1, wherein said substance includes a scent.

6. A multiple scent delivery device of claim 1, wherein said heating source includes a jar having a candle therein.

7. A multiple scent delivery device of claim 6, which includes a jar connecting collar removably interconnecting said support housing and said candle jar.

8. A multiple scent delivery device of claim 1, which includes a press fit locator positionally maintaining said cone shaped inner flue in a predetermined position within said support housing.

9. A multiple scent delivery device of claim 1, which includes a hanger member operably connected to said support housing to enable said multiple scent delivery device to be hung or suspended.

10. A multiple scent delivery device of claim 1, wherein said multiple scent delivery device includes a quantity of at least one aromatic fluid.

11. A multiple scent delivery device of claim 10, wherein said aromatic fluid disperses in a vaporous form into the ambient air when heated and delivers fragrance at lower levels when the heat source is not active.

12. A multiple scent delivery device of claim 1, wherein said support housing is cylindrical and includes at least one air inlet hole in a cylinder wall adjacent said lower end.

13. A multiple scent delivery device of claim 12, wherein said cylinder wall further includes inlet hole adjacent said upper end.

14. A multiple scent delivery device of claim 1, wherein said cone shaped inner flue has holes adjacent said lower end of said cone shaped inner flue.

15. A multiple scent delivery device of claim 8, wherein said press fit locator has a width configured to friction fit within said support housing and includes a central open surface to receive said upper end of said cone shaped inner flue in a contacting manner.

16. A multiple scent delivery device of claim 1, wherein said upper container has a diameter width configured to friction fit within said support housing.

17. A multiple scent delivery device of claim 1, wherein said lower end of said cone shaped inner flue has a diameter width configured to friction fit within said support housing.

18. A multiple scent delivery device of claim 7, wherein said jar connecting collar has a diameter width configured to friction fit within said support housing.

* * * * *